United States Patent [19]

Duchesne

[11] Patent Number: 5,026,846
[45] Date of Patent: Jun. 25, 1991

[54] PROCESS FOR THE PREPARATION OF DIARYL SULPHIDES AND DIARYL SELENIDES

[75] Inventor: Jean-Pierre Duchesne, Lyons, France

[73] Assignee: Rhone-Poulenc Sante, Antony, France

[21] Appl. No.: 393,777

[22] Filed: Aug. 15, 1989

[30] Foreign Application Priority Data

Aug. 18, 1988 [FR] France .................. 88 10982

[51] Int. Cl.$^5$ ............... C07D 279/20; C07D 293/10; C07F 9/6553
[52] U.S. Cl. .......................... 544/1; 544/35; 544/37; 544/238; 544/333; 544/405; 544/375; 568/12
[58] Field of Search ............. 544/1, 35, 37, 238, 544/333, 405, 375; 568/12

[56] References Cited

U.S. PATENT DOCUMENTS 2,433,658 12/1947 Geiger ................. 260/243

FOREIGN PATENT DOCUMENTS 1029987 12/1950 France .
1058936 3/1952 France .

OTHER PUBLICATIONS

Blackburn et al Chemical Abstracts, vol. 98. No. 23, Jun. 6, 1983, p. 645, No. 198127m.

Filinova et al Chemcial Abstracts, vol. 103, No. 23, Dec. 9, 1985, p. 637 No. 195669a.
Sergeev et al Chemical Abstracts, vol. 107, No. 22, Nov. 30, 1987, p. 5, No. 199004k.

Primary Examiner—John M. Ford
Attorney, Agent, or Firm—Morgan & Finnegan

[57] ABSTRACT

Diaryl sulphides and diaryl selenides of formula:

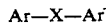

where X = S or Se and Ar = aryl are made by the action of sulphur and sulphur dioxide or selenium and selenium dioxide on a compound of formula:

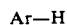

The process is especially useful for the preparation of phenothiazines of formula

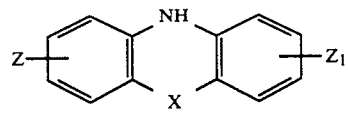

in which X=S or Se and Z and $Z_1$, which may be identical or different, are each hydrogen, halogen, alkyl or alkoxy.

6 Claims, No Drawings

PROCESS FOR THE PREPARATION OF DIARYL SULPHIDES AND DIARYL SELENIDES

FIELD OF THE INVENTION

The present invention relates to the preparation of diaryl sulphides and diaryl selenides of formula:

Ar—X—Ar  (I)

in which Ar represents an aryl radical and X represents a sulphur or selenium atom.

According to the present invention, the aforesaid diaryl sulphides and diaryl selenides are prepared by reacting an aromatic compound of formula

AR—H  (II)

in which Ar is as defined above, with sulphur or selenium and sulphur dioxide or selenium dioxide, in the proportions of half an equivalent of sulphur or selenium and half an equivalent of sulphur dioxide or selenium dioxide for each two moles of the aromatic compound used as starting material, at a temperature greater than 80° C., and isolating the diaryl sulphide or diaryl selenide obtained.

The present invention is especially useful for the preparation of optionally substituted sulphur- or selenium-containing condensed heterocycles of formula:

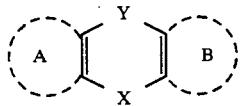  (III)

in which rings A and B, which may be identical or different, each represent a phenyl ring or a heterocyclic aromatic ring containing 1 or 2 nitrogen atoms, such as pyridyl or pyrimidyl, X is defined as above and Y represents a nitrogen or phosphorus atom (i.e. —NH— or —PH—), it being understood that when X represents a selenium atom, Y can only represent a nitrogen atom, by the action of sulphur and sulphur dioxide (SO$_2$) or selenium and selenium dioxide (SeO$_2$) on a compound of formula:

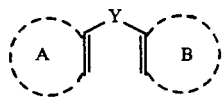  (IV)

in which rings A and B and Y are as defined above.

More particularly still, the present invention is useful for the preparation of phenothiazines or phenoselenazines of formula:

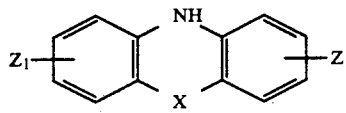  (V)

in which X is as defined above, and Z and Z$_1$, which may be identical or different, each represent one or more atoms or radicals chosen from hydrogen, halogen, alkyl, alkoxy, hydroxyl, amino, alkylamino, dialkylamino, acyl and acylamino, the said alkyl radicals and alkyl portions of the other radicals containing 1 to 4 carbon atoms each and being unsubstituted or substituted by phenyl, by the action of sulphur and sulphur dioxide or selenium and selenium dioxide on a compound of formula:

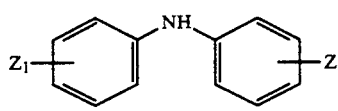  (VI)

in which Z and Z$_1$ are as defined above.

BACKGROUND OF THE INVENTION

It is known that sulphur or selenium react with aromatic compounds according to the following equation:

2Ar—H + 2X ⟶ Ar—X—Ar + H$_2$X or

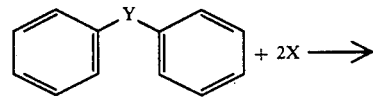

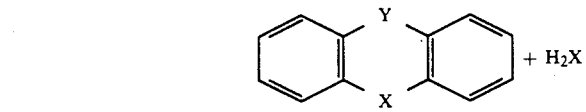

The reaction is generally catalyzed by a halogen (bromine, iodine), an aluminium halide (chloride, bromide, iodide), a ferric halide (chloride, bromide), zinc chloride or antimony chloride, as has been described, for example, in French Patents 1,029,987 or 1,058,936, or in U.S. Pat. Nos. 2,415,363 or 2,433,658.

According to the known processes, aromatic sulphides, and more particularly phenothiazines, can be obtained by reacting two moles of sulphur per mole of diphenylamine in the presence of a catalyst, the quantity of which is generally less than 3% by weight. The reaction takes place at a temperature above 120° C. The reaction kinetics increase with increasing temperature and it can be advantageous to work at a temperature of between 180° and 200° C., since a temperature greater than 200° C. leads to the formation of tars and undesirable by-products. In addition, implementation of the known processes leads to the formation of a stoichiometric quantity of hydrogen sulphide (H$_2$S).

Generally, during implementation of known processes, the reaction speed reduces considerably when the level of conversion of the diphenylamine reaches 90%. To obtain a complete reaction, it is therefore necessary to raise the temperature and to remove the hydrogen sulphide by means, for example, of an inert gas such as nitrogen, argon or carbon dioxide. Sometimes the slowing in the reaction speed can be due to a loss of catalyst, which is entrained in the effluent. Thus, when iodine, which is the catalyst which is generally used in this type of reaction, is used, there is a loss in the form of hydriodic acid. It is therefore necessary to increase the quantity of catalyst or even to add the catalyst continuously.

However, the principal drawback of the known processes lies in the production of hydrogen sulphide. In addition to the fact that the formation of the hydrogen sulphide consumes half of the sulphur used, it is necessary to remove it which entails, for industrial hygiene and environmental protection reasons, the use of costly industrial apparatus.

It has been proposed to replace the sulphur by a sulphur-containing compound such as sulphur chloride, sulphur dichloride, sodium thiosulphate, antimony or arsenic sulphide, an alkaline polysulphide, or thionyl chloride, which lead to a smaller formation of hydrogen sulphide. However, yields are then generally mediocre, and the products obtained require long and difficult purification.

DETAILED DESCRIPTION OF THE INVENTION

The process according to the present invention allows aromatic sulphides or selenides to be obtained without the formation of hydrogen sulphide or hydrogen selenide, in very good yields and with high reaction speeds.

The process according to the invention consists in treating an aromatic compound of formula (II), (IV) or (VI) in which the different symbols are defined as above, in a closed environment with a mixture of sulphur and sulphur dioxide or of selenium and selenium dioxide, the sulphur dioxide or the selenium dioxide being used in sufficient quantity to convert the hydrogen sulphide or the hydrogen selenide to sulphur or selenium. The sulphur or selenium thus regenerated takes part in the reaction again, until it has completely disappeared. The reaction can be practically quantitative without the detection of traces of hydrogen sulphide or hydrogen selenide. As a result the process according to the invention can be represented by the following equations:

$$2Ar-H + \tfrac{1}{8}X + \tfrac{1}{2}XO_2 \longrightarrow Ar-X-Ar + H_2O$$

or

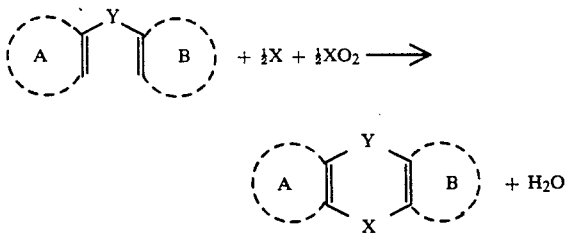

As a result, by implementing the process according to the invention, the whole of the sulphur used in the $S_8$ form and the sulphur dioxide, or of the selenium and the selenium dioxide, is consumed, and the by-product of the reaction is water, the removal of which raises no particular problems.

In the process of the invention, a stoichiometric quantity of sulphur or selenium is used with respect to the aromatic compound starting material. For example, in the case of synthesis of phenothiazines or phenoselenazines of general formula (V), 0.5 moles of sulphur or selenium is used per mole of diphenylamine of general formula (VI). If a lesser quantity is used, the reaction is incomplete, while if a greater quantity is used undesirable by-products are formed which come from the reaction of the sulphur or selenium with the phenothiazine obtained.

The quantity of sulphur dioxide or selenium dioxide which is used is at least stoichiometric with respect to the aromatic compound starting material. For example, in the case of synthesis of phenothiazines or phenoselenazines of formula (V), at least 0.5 mole of sulphur dioxide or selenium dioxide is used per mole of diphenylamine of formula (VI). Generally, a 5 to 20% excess in moles of sulphur dioxide or selenium dioxide allows the reaction speed to be increased without interfering with selectivity.

Sulphur dioxide can be used in the liquid form, in gaseous form under pressure, or in solution in a suitable organic solvent. However, the process cannot be carried out working only in liquid sulphur dioxide.

Selenium dioxide is generally used in the solid form or in solution in a suitable organic solvent.

Aluminium halides (chloride, bromide, iodide) gallium halides (chloride, bromide), lithium iodide, the quaternary ammonium iodides, sodium and potassium iodides in the presence of a strong acid such as phosphoric acid, transition-metal iodides (iron, chrome, cobalt), copper iodide, and more generally compounds permitting the liberation of an iodide or of iodine in the reaction conditions, bromine, hydrobromic acid, hydriodic acid, boron trifluoride and preferably iodine, can be used as catalysts. Generally, a quantity of catalyst representing from 0.04 to 50% in moles with respect to the starting material is used; the quantity of catalyst can be a function of its sensitivity to the water liberated during the reaction.

Generally, using iodine as catalyst, the reaction speed is directly linked to the quantity of iodine used and, in the case of the preparation of substituted cyclic compounds which can exist in several isomeric forms, the selectivity can diminish as a function of the increase in the quantity of iodine used. In addition, the nature of the substituents can influence the course of the reaction. Thus, electron-donor substituents have a tendency to favor the reaction and, because of this, it could be possible to implement the process with smaller quantities of catalyst.

For implementation of the process according to the invention, the temperature is greater than 80.C and is generally between 130° and 280° C. In the case of preparation of phenothiazines of formula (V), it is particularly important to work at a temperature lower than 200° C. in order to avoid formation of undesirable by-products. Generally, the optimum temperature of the reaction is a function of the nature of the aromatic compound used, of the nature and quantity of the catalyst used and of the presence or absence of a solvent.

In the particular case of cyclization of diphenylamines of general formula (VI) one of the phenyl rings of which is substituted in the 3-position, implementation of the process generally results in the phenothiazine substituted in the 2-position (I.U.P.A.C. nomenclature) when working at low temperature, and in the phenothiazine substituted in the 4-position when working at a high temperature. Depending on the reaction temperature it is possible to obtain a mixture of isomers in the 2- and 4-positions.

Generally, the process is implemented in bulk with the reagents maintained in the liquid state at the reaction temperature. However, it can be advantageous to work in a suitable solvent which has the property of dissolving the starting aromatic compounds, the reagents and the reaction products in order to obtain a homogeneous medium. Generally the solvents are chosen from the solvents which are chemically inert in the conditions of implementation of the process. Particularly suitable solvents are chosen from the saturated aliphatic or alicyclic hydrocarbons containing 10 to 16 carbon atoms, such as decalin or bicyclohexyl, optionally substituted by one or several alkyl radicals containing 1 to 4 carbon atoms, or, preferably, from the aprotic non-basic polar solvents such as the dialkyl sulphones which contain less than 10 carbon atoms, or sulpholane (tetrahydrothiophene-1,1-dioxide).

Generally, the process is implemented in a closed reactor under autogenous pressure which, depending on the reaction conditions, is less than 5 bars at the start of the reaction.

The reaction time can be between 30 minutes and 5 hours, depending on the nature and the quantity of the products used, on the temperature and on the nature of the solvent.

The reaction products are isolated by applying the normal methods such as precipitation and recrystallization from a suitable solvent.

The products obtained by implementation of the process according to the invention, and in particular the phenothiazines and the phenoselenazines, are particularly useful for preparation of therapeutically active products.

EXAMPLES

The following Examples illustrate the invention.

EXAMPLE 1

3-Methoxydiphenylamine (1.00 g, 5 mmoles), sulphur (0.08 g, 2.5 mmoles), sulphur dioxide (0.2 g, 3.12 mmoles) and iodine (0.00254 g, 0.001 mmole) in solution in sulpholane (4 cc) are introduced into a 25 cc tube under an atmosphere of nitrogen. The tube is sealed and then heated for 2 hours to 165° C.

The reaction mixture is diluted with water (15 cc). The product which precipitates is separated by filtration. A product containing 2-methoxyphenothiazine (0.958 g: 83%) is thus obtained.

The following are found in the mother liquor:
3-methoxydiphenylamine (0.003 g)
4-methoxyphenothiazine (0.050 g).

The conversion rate of the 3-methoxydiphenylamine is 91%, and the chemical yield of 2-methoxyphenothiazine is 91%.

EXAMPLE 2

Diphenylamine (1 g, 5.92 mmoles), sulphur (0.095 g, 2.97 mmoles), sulphur dioxide (0.230 g, 3.60 mmoles) and iodine (0.004 g), in solution in sulpholane (3 cc), are introduced into a 25 cc tube under an atmosphere of nitrogen. The tube is sealed and then heated for 5 hours to 180° C. under autogenous pressure.

After cooling, the mixture is taken up in methylene chloride. The following are found by high performance liquid chromatography (HPLC):
diphenylamine (0.070 g)
phenothiazine (1.09 g)

The conversion rate of the diphenylamine is 93%, and the yield of phenothiazine is 99% with respect to the diphenylamine converted.

EXAMPLE 3

3-Chlorodiphenylamine (1.00 g, 4.99 mmoles), sulphur (0.080 g, 2.50 mmoles), sulphur dioxide (0.190 g, 2.97 mmoles) and iodine (0.0125 g, 0.049 mmoles), in solution in sulpholane (1 cc), are introduced into a 25 cc tube under an atmosphere of nitrogen. The tube is sealed and then heated for 4 hours to 160° C. under autogenous pressure. After cooling, the mixture is taken up in methylene chloride.

The following are found by high performance liquid chromatography;
3-chlorodiphenylamine (0.200 g)
2-chlorophenothiazine (0.579 g)
4-chlorophenothiazine (0 248 g).

The conversion rate of the 3-chlorodiphenylamine is 80%, and the yield of 2-chlorophenothiazine is 63% with respect to the 3-chlorodiphenylamine converted.

EXAMPLE 4

N-phenyl-3-aminopyridine (0.510 g, 3.0 mmoles), sulphur (0.048 g, 1.50 mmoles), sulphur dioxide (0.145 g) and iodine (0.0076 g, 0.03 mmoles), in solution in toluene (4 cc), are introduced into a 25 cc tube under an atmosphere of nitrogen. The tube is sealed and then heated for 2 hours to 260° C. under autogenous pressure. After cooling, analysis of the reaction mixture by nuclear magnetic resonance at 200 MHz shows that:
the conversion rate of the N-phenyl-3-aminopyridine is about 50%,
the yield of 4-aza-phenothiazine is about 20%, and
the yield of 2-aza-phenothiazine is about 20%.

EXAMPLE 5

Diphenylamine (0.506 g, 3 mmoles), selenium dioxide (SeO$_2$) (0.200 g, 1.80 mmoles), selenium (0.119 g, 1.5 mmoles) and iodine (25 mg, 0.1 mmole), in solution in sulpholane (4 cc), are introduced into a 25 cc tube under an inert atmosphere. The tube is sealed and then heated for 4 hours to 200° C. The reaction mixture is taken up in an ethanolmethylene chloride mixture. Measurement by high performance liquid chromatography (HPLC) shows that the conversion rate is about 40% and that the yield of phenoselenazine is about 38%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A process for the preparation of a product of formula:

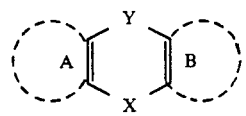

in which rings A and B, which may be identical or different, each represent a phenyl ring which may be substituted by one or more atoms or radicals selected from the class consisting of hydrogen, halogen, alkyl, alkoxy, hydroxyl, amino, alkylamino, dialkylamino, acyl and acylamino, the said alkyl radicals and alkyl portions of the other radicals containing 1 to 4 carbon atoms each and being unsubstituted or substituted by phenyl, or a six-membered heterocyclic aromatic ring containing 1 or 2 nitrogen atoms, and Y represents —NH— or —PH—, and X represents sulphur or selenium, it being understood that Y can only represent —NH— when X is selenium, which comprises reacting an aromatic compound of formula:

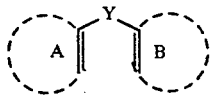

in which A, B and Y are as defined above, with sulphur or selenium and sulphur dioxide or selenium dioxide in the proportions of half an equivalent or sulphur or selenium and half an equivalent of sulphur dioxide or selenium dioxide for each mole of the starting aromatic product, at a temperature greater than 80° C., optionally in the presence of a catalyst, and isolating the product obtained.

2. A process according to claim 1, wherein the reaction is carried out in the presence of, as catalyst, an aluminum or gallium halide, lithium, sodium or potassium iodide, a quaternary ammonium iodide, an iron, chromium, cobalt or copper iodide, a compound which liberates an iodide or iodine under the reaction conditions, hydrobromic or hydriodic acid, bromine or iodine.

3. A process according to claim 2, wherein the catalyst is iodine.

4. A process according to claim 1, wherein it is carried out in an organic solvent which is a saturated aliphatic or cycloaliphatic hydrocarbon of 10 to 16 carbon atoms, a dialkyl sulphone of less than 10 to 16 carbon atoms, a dialyl sulphone of less than 10 carbon atoms, or sulpholane.

5. A process according to claim 1, wherein it is carried out at a temperature between 130° to 280° C.

6. A process according to claim 1, wherein it is carried out under autogenous pressure.

* * * * *